United States Patent
Delledonne et al.

(10) Patent No.: US 9,334,450 B2
(45) Date of Patent: May 10, 2016

(54) PROCESS FOR THE CONVERSION OF LIGNIN TO LIQUID HYDROCARBONS

(75) Inventors: Daniele Delledonne, Oleggio (IT); Roberto Buzzoni, Chivasso (IT); Daniele Bianchi, Arese (IT)

(73) Assignee: ENI S.p.A., Rome (IT)

( * ) Notice: Subject to any disclaimer, the term of this patent is extended or adjusted under 35 U.S.C. 154(b) by 891 days.

(21) Appl. No.: 13/636,797

(22) PCT Filed: Mar. 17, 2011

(86) PCT No.: PCT/IB2011/000591
§ 371 (c)(1),
(2), (4) Date: Nov. 15, 2012

(87) PCT Pub. No.: WO2011/117705
PCT Pub. Date: Sep. 29, 2011

(65) Prior Publication Data
US 2013/0060071 A1  Mar. 7, 2013

(30) Foreign Application Priority Data
Mar. 24, 2010 (IT) .............. MI2010A0489

(51) Int. Cl.
C07C 1/00 (2006.01)
C10G 3/00 (2006.01)
C07C 37/54 (2006.01)
(Continued)

(52) U.S. Cl.
CPC . *C10G 3/50* (2013.01); *C07C 37/54* (2013.01); *C10G 1/002* (2013.01); *C10G 1/06* (2013.01); *C10G 3/46* (2013.01); *C10G 3/47* (2013.01); *C10G 3/48* (2013.01); *C10L 1/04* (2013.01); *C10G 2300/1014* (2013.01); *C10G 2300/4006* (2013.01); *C10G 2300/4018* (2013.01);*C10G2300/44* (2013.01); *C10G 2400/02* (2013.01); *C10G 2400/06* (2013.01); *Y02P 30/20* (2015.11)

(58) Field of Classification Search
CPC .......... C10G 2300/70; C10G 2300/20; C10G 2300/1011; C10L 5/442; C10L 2300/04; C10L 220/0484
USPC ....................... 585/240, 242; 44/60
See application file for complete search history.

(56) References Cited

U.S. PATENT DOCUMENTS 3,223,698 A * 12/1965 Oshima ............... C08H 6/00
530/503
4,155,832 A   5/1979 Cox et al.
(Continued)

FOREIGN PATENT DOCUMENTS

WO     2008 039756     4/2008

OTHER PUBLICATIONS

International Search Report Issued Mar. 27, 2012 in PCT/IB11/000591 Filed Mar. 17, 2011.

*Primary Examiner* — Nina Bhat
(74) *Attorney, Agent, or Firm* — Oblon, McClelland, Maier & Neustadt, L.L.P.

(57) ABSTRACT

A process for the conversion of lignin to liquid hydrocarbons comprising:
(1) hydrogenolyzing a lignin in the presence of at least one hydrogenolysis catalyst, at a temperature ranging from 250° C. to 350° C., preferably ranging from 290° C. to 320° C., to obtain depolymerized lignin; and (2) hydrodeoxygenating said depolymerized lignin in the presence of a hydrodeoxygenating catalyst to obtain a mixture of liquid hydrocarbons. The resultant liquid hydrocarbons can be used as such (biofuels) for the production of reformulated gasolines, or they can be used for the production of gasolines or oils by conventional refining processes.

47 Claims, 3 Drawing Sheets

(51) Int. Cl.
 *C10G 1/00* (2006.01)
 *C10G 1/06* (2006.01)
 *C10L 1/04* (2006.01)

(56) References Cited

U.S. PATENT DOCUMENTS

| | | | | |
|---|---|---|---|---|
| 4,420,644 A * | 12/1983 | Huibers | ............... | C07C 37/54 568/799 |
| 4,647,704 A * | 3/1987 | Engel | ............... | C07C 37/52 568/716 |
| 5,959,167 A * | 9/1999 | Shabtai | ............... | C10G 1/002 585/240 |
| 6,172,272 B1 * | 1/2001 | Shabtai | ............... | C10G 1/002 208/108 |
| 2008/0076945 A1 * | 3/2008 | Marker | ............... | C10G 1/083 568/426 |
| 2008/0299021 A1 | 12/2008 | Boykin et al. | | |
| 2008/0312346 A1 | 12/2008 | McCall et al. | | |
| 2009/0326285 A1 | 12/2009 | Bauer et al. | | |
| 2011/0065814 A1 * | 3/2011 | Matson | ............... | C01B 3/22 518/702 |

* cited by examiner

PROCESS FOR THE CONVERSION OF LIGNIN TO LIQUID HYDROCARBONS

This application is the 371 National Stage of PCT/IB2011/000591, filed Mar. 17, 2011. Applicant's claim benefit of Italian Application MI2010A 00489, filed Mar. 24, 2010, under 35 U.S.C. 119.

The present invention relates to a process for the conversion of lignin to liquid hydrocarbons.

More specifically, the present invention relates to a process for the conversion of lignin to liquid hydrocarbons which comprises subjecting the lignin to hydrogenolysis so as to obtain depolymerized lignin and subjecting said depolymerized lignin to hydrotreating so as to obtain a mixture of liquid hydrocarbons.

Said liquid hydrocarbons can be used as such (biofuels), for the production of reformulated gasolines, or they can be used for the production of gasolines or of gas oils through conventional refining processes.

A reduction in oil reserves on the one hand, and the continuous increase in consumptions of oil products on the other, require a search for and the exploitation of new raw materials alternative to petroleum and the implementation of new technologies for their production. In this scenario, the development and production of fuels from alternative sources are fundamental, i.e. of fuels used in any type of transport such as, for example, air, ship, automobile, which are responsible for the consumption of over 60% of extracted oil. Among alternative sources, biomasses of a vegetable origin (a category which belongs to the so-called renewable energy sources), can be mentioned.

Among biomasses of a vegetable origin useful for the production of biofuels, the following can be listed:
  cultivations of cereals, such as maize, wheat, barley, from which bioethanol, which can be used as such as a substitute for traditional gasolines or in a mixture with said traditional gasolines, can be obtained through the fermentation of starches;
  cultivations of vegetable species with a high content of triglycerides or of oils (i.e. oleaginous species), such as, for example, rape, soya, sunflower, palm oils, from which biodiesel can be obtained.

Recently, with the development of new technologies such as, for example, new fermentation technologies, lignocellulosic biomasses have also been added to said biomasses of a vegetable origin useful for the production of biofuels.

The use of lignocellulosic biomasses in the production of biofuels (in particular, bioethanol from cellulose) is advantageous from numerous points of view with respect to the use of the cultivations of cereals and of oleaginous species mentioned above, as:
  (i) they are widely available, for example as waste products of the wood and food industry, and also of the crops reported above;
  (ii) they are inexpensive;
  (iii) they do not compete with cultivated products for human nutrition, even if they at least partly compete with cultivated products for animal nutrition and for the use of cultivated land.

Although various processes are known for the transformation into bioethanol of both the cellulose fraction and hemicellulose fraction of lignocellulosic biomasses (these fractions together generally represent about 60% by weight-70% by weight of the whole lignocellulosic biomass), lignin, which generally represents about 15%-30% by weight of the whole lignocellulosic biomass, remains excluded.

The commercial implementation of bioethanol production processes from cellulose and hemicellulose currently envisages the use of lignin as a low-value solid fuel for the production of utilities such as, for example, steam and electricity, which can be used in the same bioethanol production plant or, optionally, can be sold to external sources (e.g., electricity) as described, for example, by Fernando et al. in the following article: "Biorefineries: Current Status, Challenges, and Future Direction", published in "Energy & Fuels" (2006), Vol. 20, pages 1727-1737.

Lignin is generally defined as the constituent which holds together the various vegetable fibres (e.g., linear fibres of cellulose) in vegetable organisms, giving them compactness and resistance and also provides protection against insects, pathogenic agents, lesions and ultraviolet light. Chemically, it is a high-molecular-weight, three-dimensional, cross-linked polymer, comprising $C_9$ methoxy-substituted monomeric units and its raw molecular formula, approximated, can be schematized as follows: $C_{10}H_{12}O_3$.

Lignin has a relatively low oxygen content if compared, for example, with the oxygen content of cellulose, said oxygen content being, in fact, on an average, about 25%-30% by weight with respect to the total weight of the lignin.

The transformation of lignin towards products having a higher added value such as, for example, fuels or hydrocarbons, is desirable as it would increase the quantity of biofuels which can be obtained from lignocellulosic biomasses.

The transformation of lignin to fuels has already been faced in the art and the same techniques normally used for the treatment of lignocellulosic biomasses were substantially used, such as, for example:
  high-temperature pyrolysis (gasification), for producing synthesis gas, i.e. carbon monoxide (CO) and hydrogen ($H_2$), which, in turn, after purification, can be converted to a hydrocarbon fraction by means of the Fischer-Tropsch process; the use of lignin as starting material of said pyrolysis, however, has the disadvantage of causing a higher formation of carbonaceous residues with respect to the pyrolysis of lignocellulosic biomasses as such (i.e. of lignocellulosic biomasses comprising cellulose, hemicellulose and lignin), as described for example by Haiping Yang et al. in the article "Characteristics of hemicellulose, cellulose and lignin pyrolysis", published in "Fuel" (2007), Vol. 86, pg. 1781-1788;
  pyrolysis for producing liquid products, which converts lignin into a liquid product, called bio-oil, which is unstable and of a low quality, unsuitable for being used directly as fuel or in refinery due to the high oxygen content as described, for example, by R. Fahmi et al. in the article "The effect of lignin and inorganic species in biomass on pyrolysis oil yields, quality and stability", published in "Fuel" (2008), Vol. 87, pg. 1230-1240;
  liquefaction and direct catalytic hydrodeoxygenation of lignin to products which can enter directly into the refining cycle.

Whereas the first two processes (i.e. high-temperature pyrolysis and pyrolysis for producing liquid products) are substantially a concatenation of distinct processes known in the art in a multistep process, in the best of cases at least two steps, the third process (i.e. liquefaction), at least in some embodiments, can be considered a single-step process.

The liquefaction of lignin was already faced immediately after the second World War, with the main objective of obtaining some chemical products of the group of phenols, with a high yield, to be used in organic synthesis. A great deal of patent literature, of which some examples are provided hereunder, is in fact focused on the synthesis of phenols, in particular, of phenol and only incidentally on the production of hydrocarbons.

American U.S. Pat. No. 2,870,133, for example, describes a process for the decomposition of lignin, preferably coming from the saccharification of wood, into distillable products containing a substantial quantity of phenols, which comprises mixing lignin with xylenol as liquid dispersing agent and iron sulfate as hydrogenation catalyst so as to form a thin paste; feeding said thin paste in continuous at high pressure to a reaction chamber maintained at a temperature higher than 250° C. and at a pressure higher than 300 atmospheres (about 30 MPa), preferably at about 700 atmospheres (about 70 MPa); sending hydrogen in continuous to said reaction chamber and reacting said thin paste and said hydrogen in said reaction chamber so as to decompose the lignin into distillable products; separating the liquid fractions from the gaseous fractions immediately after the reacted mixture has been discharged from the reaction chamber, and distilling the liquid fractions so as obtain the above distillable products. The process described above is said to allow a conversion of the lignin practically close to 100%, obtaining about 60% of distillable products.

American U.S. Pat. No. 4,731,491 describes a process for the liquefaction of lignin deriving from the Kraft process which comprises forming in situ a catalytic composition resulting from the addition of a sulfur source to an aqueous solution of divalent iron, and at least one promoter metal selected from the group consisting of copper, tin, silver, chromium, cobalt, nickel, zinc, molybdenum, gallium and germanium, and reacting an aqueous mixture of said lignin, phenol and an aliphatic alcohol having a low number of carbon atoms, in the presence of said catalytic composition, in an atmosphere of hydrogen, at a temperature ranging from about 300° C. to about 450° C. and at an initial pressure ranging from about 50 atmospheres (about 5 MPa) to about 150 atmospheres (about 15 MPa). The process described above is said to allow the production of cresol in a quantity equal to about 45% and a mixture of $C_6$-$C_9$ monophenols in a quantity equal to about 65%, with a consequent substantial improvement in the economical return of the liquefaction of lignin.

American U.S. Pat. No. 4,647,704 describes a hydrocracking process of lignin to produce hydroxy-aromatic compounds, which comprises reacting a solution of non-basic lignin with hydrogen, at a pressure ranging from about 500 psgi (about 3.4 MPa) to about 3500 psgi (about 24.1 MPa) and at a temperature ranging from about 300° C. to about 450° C., in the presence of a supported hydrocracking catalyst, said catalyst being composed of about 2% by weight to about 20% by weight of tungsten oxide or tungsten sulfide and, optionally, a second component selected from the group consisting of nickel, palladium and cobalt, the weight ratio between said tungsten and said second component ranging from about 1:1 to about 100:1, said tungsten and said optional second component being deposited on a carrier selected from the group consisting of alumina, silica, silica-alumina, aluminium phosphate, silica-aluminium phosphate, zirconium, titanium, lanthanum phosphate, and combinations thereof, and recovering the reaction product. The process described above is said to allow the production of phenols with a high yield.

In the article "Catalytic hydrotreatment of some technical lignins", published in "Bioresource Technology" (1993), Vol. 45, Issue 3, pages 189-194, Oasmaa et al. describe a characterization study of the oil obtained by the liquefaction of lignin through hydrotreating, carried out in the presence of commercial hydrocracking catalysts, at 400° C., in the presence of hydrogen and at a pressure equal to 10 MPa. Oasmaa et al. observed an oil yield equal to 65%. Of said oil, about 10% by weight proved to be composed of aromatic monocyclic products, of which only 1% of alkyl benzenes, the remaining part being phenols. The remaining part of said oil comprises a small part of aromatic polycyclic products and a significant part of products deriving from the partial demolition of lignin as also described, for example, by R. W. Thring et al. in the article "Hydrocracking of solvolysis lignin in a batch reactor", published in "Fuel" (1996), Vol. 75, pages 795-800.

The processes reported above however can have various drawbacks. In particular, these processes generally produce low quantities of deoxygenated products (i.e. hydrocarbons). The products obtained with these processes, in fact, generally have an average oxygen content higher than 15%: this makes them unsuitable for being fed to traditional refinery processes for the production of fuels.

Efforts have therefore been made in the art for obtaining higher quantities of hydrocarbons from the liquefaction of lignin.

American U.S. Pat. No. 5,959,167, for example, describes a process for converting lignin into reformulated hydrocarbon gasoline comprising the steps of: (a) supplying lignin; (b) subjecting the lignin to depolymerization catalyzed by bases (e.g., sodium hydroxide, potassium hydroxide), in the presence of supercritical alcohol (e.g., methanol, ethanol) as reaction medium; and (c) subjecting the depolymerized lignin to hydroprocessing to produce reformulated hydrocarbon gasoline. The recovery of the depolymerized lignin envisages neutralization of the base with hydrochloric acid. The hydroprocessing treatment of the depolymerized lignin is carried out in a single step thanks to the use of two different catalysts, in sequence, operating under increasing operative conditions in terms of temperature and hydrogen pressure, passing from one catalyst to the other. The process described above is said to be capable of producing a mixture of cyclohexanes, alkylated cyclopentanes, $C_7$-$C_{11}$ alkylbenzenes and $C_5$-$C_{12}$ branched paraffins, substantially free of benzene.

American patent application US 2003/0100807 describes a process for the conversion of biomass into an additive for oil or fuels deriving from oil comprising: (a) extracting a fraction containing lignin from a biomass operating in a reaction medium so as to obtain lignin; (b) subjecting the lignin to depolymerization in the presence of an aqueous solution of a base (e.g., sodium hydroxide) and/or of a solid superbase (e.g., zeolite of the type CsX) in order to obtain a first composition comprising depolymerized lignin; (c) subjecting said first composition to hydroprocessing in order to obtain a second composition, wherein said sec- and composition provides an additive for oil or fuels deriving from oil. Said additive is a mixture of $C_7$-$C_{10}$ alkylbenzenes capable of increasing the octane number of fuels deriving from oil (e.g., gasoline). The process described above is said to be capable of giving a high yield of $C_7$-$C_{10}$ alkylbenzenes. The mixture obtained is said to comprise a quantity ranging from 75% by weight to 95% by weight of said $C_7$-$C_{10}$ alkylbenzenes and a quantity ranging from 5% by weight to 25% by weight of $C_5$-$C_{10}$ branched paraffins and $C_6$-$C_7$ alkyl-substituted naphthenes.

American patent application US 2008/0050792 describes a process for the conversion of lignin to biofuel comprising: (a) subjecting the lignin to depolymerization catalyzed by bases (e.g., sodium hydroxide, potassium hydroxide), in the presence of a solvent (e.g., methanol, ethanol, water), in order to obtain partially depolymerized lignin; (b) subjecting the partially depolymerized lignin to stabilization/partial hydrodeoxygenation in order to obtain a partially hydrodeoxygenated product; (c) reacting the product obtained in step (b) in a hydroprocessing step in order to obtain biofuel. The process described above, in particular the production of the partially hydrodeoxygenated product in step (b) is said to be capable of reducing or even preventing the formation of polymeric solids which can cause the blockage of the reactor and coking of the catalyst.

Yan N. et al., in the article "Selective degradation of Wood Lignin over Noble-Metal Catalysts in a Two-Step Process", published in ChemSusChem (2008), Vol. 1, pages 626-629, describe a two-step process for the conversion of lignin to alkanes and methanol. In particular, the sawing of pre-extracted birch wood is subjected to hydrogenolysis in the presence of a catalyst, preferably of a catalyst supported on coal such as, for example, Pt/C, Ru/C, Pd/C, Rh/C, in the presence of hydrogen, at a temperature of 473 K (about 200° C.) and at a pressure of 4 MPa, for 4 hours. After hydrogenolysis, the mixture is subjected to hydrogenation, in the presence of a catalyst, preferably of a catalyst supported on coal such as, for example, Pd/C, Ru/C, Pt/C, in the presence of phosphoric acid, at a temperature of 523 K (about 250° C.), at a pressure of 4 MPa, for a time ranging from 30 minutes to 2 hours.

Also the processes described above, however, can have various drawbacks.

In the case of the use of alcohol in the depolymerization step of lignin, said alcohol can become incorporated in the depolymerized lignin causing an excessive consumption of solvent (i.e. of alcohol) and a consequent increase in the production costs. Furthermore, the oxidation of the alcohols to acids can take place with a consequent consumption of the base, slowing down the depolymerization reaction of the lignin, as described, for example, by J. Miller et al. in the technical report "SAND2002-1317", of the US Department of Energy (USA), relating to: "Batch Microreactor Studies of Lignin Depolymerization by Bases. 1. Alcohol Solvents", (2002), DOI 10.2172/800959.

In addition, in the case of the depolymerization of lignin in the presence of a base, the use of hydrochloric acid should be considered for the neutralization of the base used, hydrochloric acid which is generally used in such quantities as to obtain a pH value equal to about 2, with the relative formation of salts which must be disposed of.

Furthermore, the use of water instead of alcohol in the depolymerization of lignin can reduce the conversion of the lignin as described, for example, by J. Miller et al. in the technical report "SAND2002-1317", of the US Department of Energy (USA), relating to: "Batch Microreactor Studies of Lignin Depolymerization by Bases. 1. Aqueous Solvents", (2002), DOI 10.2172/800964.

In the case of the hydrogenolysis of lignin in the presence of a catalyst supported on coal, such as, for example, Pt/C, Ru/C, Pd/C, Rh/C, moreover, the addition of phosphoric acid is suggested for improving the conversion of lignin. Said phosphoric acid can cause damage to the plant not only as free acid that can cause, for example, corrosion phenomena, but also in the form of salts (e.g., insoluble phosphates) which can optionally be formed by the inorganic fraction of lignin and which can cause encrustations, for example, with a consequent increase in the production costs.

The Applicant has therefore considered the problem of finding a process for the conversion of lignin to liquid hydrocarbons with good yields capable of overcoming the drawbacks described above.

The Applicant has now found that by carrying out the hydrogenolysis of lignin at a particular temperature, it is possible to obtain a conversion of lignin to liquid hydrocarbon with a high yield.

In particular, the Applicant has found that by subjecting lignin to hydrogenolysis, in the presence of at least one catalyst, at a temperature higher than or equal to 250° C., it is possible to obtain a high conversion of the lignin to depolymerized lignin (i.e. a conversion higher than or equal to 95% by weight with respect to the total weight of the starting lignin). The depolymerized lignin thus obtained is subsequently subjected to hydrotreating to obtain liquid hydrocarbons with a high yield (i.e. a yield higher than or equal to 45% by weight with respect to the total weight of the depolymerized lignin subjected to hydrotreating).

In particular, said process allows a mixture of liquid hydrocarbons to be obtained, comprising: (i) a fraction comprising liquid hydrocarbons having a boiling point lower than 200° C. which can be used as such as biofuels, or for the production of reformulated gasolines; (ii) a fraction comprising liquid hydrocarbons having a boiling point higher than or equal to 200° C. which have an oxygen content lower than 2% by weight, preferably lower than 1% by weight, which can be fed to traditional refinery processes for the production of gasolines or gas oils (for example, to the hydrocracking section).

An object of the present invention therefore relates to a process for the conversion of lignin to liquid hydrocarbons comprising:
subjecting the lignin to hydrogenolysis in the presence of at least one hydrogenolysis catalyst, at a temperature ranging from 250° C. to 350° C., preferably ranging from 290° C. to 320° C., so as to obtain depolymerized lignin;
subjecting said depolymerized lignin to hydrotreating so as to obtain a mixture of liquid hydrocarbons.

For the purposes of the present description and of the following claims, the definitions of the numerical ranges always comprise the extremes unless otherwise specified.

As it is known in the art, the term "hydrotreating" covers a wide range of catalytic processes which use hydrogen and are widely used in the refining industry, with objectives ranging from the saturation of unsaturated hydrocarbon, both olefinic and aromatic, (hydrogenation—HYD), to the removal, from various oil fractions, of undesired elements such as, for example, oxygen (hydrodeoxygenation—HDO), sulfur (hydrodesulfuration—HDS), nitrogen (hydrodenitrogenation—HDN), vanadium and nickel (hydrodemetalization—HDM).

For the purposes of the present description and of the following claims, the term "hydrotreating" refers to the catalytic process for the removal of oxygen from depolymerized lignin, i.e. the hydrodeoxygenation process (HDO) of said depolymerized lignin. It should also be noted that by operating under the operative conditions according to the present invention, in addition to the hydrodeoxygenation process reported above, the hydrogenation (HYD) and/or the hydrocracking of said depolymerized lignin can also take place, as secondary reactions.

For the purposes of the present invention, any type of lignin, of any origin, known in the art, can be used.

According to a preferred embodiment of the present invention, said lignin can be selected from Organosolv lignins. Organosolv lignins can be prepared through a separation process from cellulose which comprises the use of an organic solvent such as, for example methanol, ethanol, propanol, isopropanol, butanol, methyl acetate, ethyl acetate, ketones, glycerol, formic acid, acetic acid, phenols, cresols, or mixtures thereof, optionally in the presence of an inorganic acid such as, for example, sulfuric acid, phosphoric acid, or mixtures thereof, as catalyst.

Greater details relating to processes for the preparation of Organosolv lignins can be found, for example, in the doctoral thesis of Esa Muurinen "Organosolv pulping—A review and distillation study related to peroxyacid pulping" (2000), Oulu University Library, ISBN 95142-5661

Among Organosolv lignins, Acetosolv lignin can be mentioned, for example, which is obtained by means of a separation process of cellulose from lignin which uses acetic acid as solvent. Greater details relating to the preparation process of said lignin can be found in the article of X. Pan et al. "Acetic acid pulping of wheat straw under atmospheric pressure", published in "Journal of Wood Science" (1999), Vol. 45 (4), pages 319-325.

According to a further embodiment of the present invention, said lignin can be selected from Kraft lignins which are by-products deriving from the paper processing industry.

According to another embodiment of the present invention, said lignin can be selected from: lignins deriving as by-product from the production processes of ethanol from lignocellulosic biomasses; lignins deriving from agricultural products or waste products deriving from the processing of said agricultural products; lignins deriving from solid urban waste.

According to a preferred embodiment of the present invention, said hydrogenolysis catalyst can be selected from supported catalysts having formula (I), (II), (III), or (IV):

$$M^1/C \qquad (I),$$

$$M^1/Al_2O_3 \qquad (II),$$

$$M^2/SiO_2 \qquad (III),$$

$$M^2/Al_2O_3 \qquad (IV),$$

wherein $M^1$ is a metal selected from palladium, ruthenium, platinum, and $M^2$ is nickel.

In addition to the carriers reported in the above formulae (I), (II), (III) and (IV), i.e. materials based on coal in the case of hydrogenolysis catalysts having formula (I), silica in the case of hydrogenolysis catalysts having formula (III), alumina in the case of hydrogenolysis catalysts having formula (II) and (IV), other carriers can be used such as, for example, mixed silica-alumina oxides, aluminium silicates, amorphous or crystalline, materials based on spinels having the formula $AB_2O_4$ wherein A is a bivalent metal ion such as, for example, bivalent iron, magnesium, zinc, manganese, nickel, whereas B is a trivalent metal ion such as, for example, aluminium, trivalent iron, chromium. Carriers based on mixtures of the inorganic materials reported above, well-known in the state of the art, can be equally used. The coal-based materials are preferably selected from activated carbons coming from natural coals or coals of a fossil origin deriving, for example, from wood, lignite, peat, coconut. Said activated carbons preferably have a surface area higher than 100 m$^2$/g, more preferably higher than 300 m$^2$/g, even more preferably higher than 600 m$^2$/g, and a low ash content.

In the above hydrogenolysis catalysts having formula (I), or (II), the metal content ($M^1$) preferably ranges from 1% by weight to 10% by weight with respect to the total weight of the hydrogenolysis catalyst whereas, in the above catalysts having formula (III), or (IV), the metal content ($M^2$) can range from 1% by weight to 65% by weight with respect to the total weight of the hydrogenolysis catalyst.

Hydrogenolysis catalysts having formula (I), (II), (III), or (IV), of the type described above, which can be used according to the present invention, are products known with the trade-names ESCAT 10 (Pd/C), ESCAT 14 (Pd/Al$_2$O$_3$), Ni-6458 (Ni/SiO$_2$) of Engelhard (now Basf).

For the purposes of the present invention, said process can be carried out batchwise, or in continuous, preferably in continuous.

For the purposes of the present invention, said hydrogenolysis can be carried out batchwise, or in continuous, preferably in continuous.

When the hydrogenolysis is carried out batchwise, for example in a heated and stirred autoclave, said hydrogenolysis catalyst can be used in an amount ranging from 0.1% by weight to 20% by weight, preferably from 1% by weight to 15% by weight, with respect to the total weight of said lignin.

According to a preferred embodiment of the present invention, said hydrogenolysis carried out batchwise, can be carried out in the presence of a solvent.

According to a preferred embodiment of the present invention, said solvent can be selected, for example, from:
  low-boiling solvents having a boiling point lower than or equal to 120° C., preferably ranging from 50° C. to 110° C., such as, for example: water; methanol; ethanol; propanol; isopropanol; methyl acetate; ethyl acetate; acetone; methyl ethyl ketone; or mixtures thereof; preferably water; methanol; ethanol; isopropanol; acetone; or mixtures thereof;
  hydroxy-aromatic solvents having a boiling point higher than or equal to 150° C., preferably ranging from 170° C. to 350° C., such as, for example: phenol; cresol; 2-methoxy-4-ethyl-phenol; 2-methoxy-4-(2-propyl)-phenol; mixtures of phenols, alkyl phenols and methoxy alkyl phenols deriving from the hydrogenolysis of lignin carried out batchwise, or in continuous; or mixtures thereof; preferably mixtures of phenols, alkyl phenols and methoxy alkyl phenols deriving from the hydrogenolysis of the lignin carried out batchwise, or in continuous.

According to a preferred embodiment of the present invention, said solvent can be used in such a quantity as to have a solvent/lignin weight ratio lower than or equal to 20/1, preferably ranging from 15/1 to 0.5/1.

According to a preferred embodiment of the present invention, said hydrogenolysis carried out batchwise, can be carried out at a partial hydrogen pressure ranging from 1 MPa to 20 MPa, preferably ranging from 3 MPa to 15 MPa.

According to a preferred embodiment of the present invention, said hydrogenolysis carried out batchwise, can be carried out for a time ranging from 9 minutes to hours, preferably ranging from 18 minutes to 5 hours.

At the end of said hydrogenolysis carried out batchwise, a mixture comprising a liquid phase, a solid phase and a gas phase is obtained. The gas phase can be separated from the liquid phase and from the solid phase by means of techniques known in the art, for example by depressurization of the autoclave in which said hydrogenolysis of lignin is carried out batchwise. Said liquid phase can be separated from said solid phase by techniques known in the art, for example by filtration or decanting.

Said liquid phase comprises, depending on the solvent used in the hydrogenolysis carried out batchwise, either all or part of the depolymerized lignin, whereas said solid phase comprises the catalyst and the optional part of the depolymerized lignin not included in said liquid phase.

When the hydrogenolysis carried out batchwise, is carried out in the presence of a low-boiling solvent (e.g., methanol, acetone), said liquid phase can be subjected to evaporation to recover and recycle said low-boiling solvent to said hydrogenolysis carried out batchwise. The residue which remains after said evaporation comprising the depolymerized lignin can be subjected to hydrotreating.

When said hydrogenolysis carried out batchwise, is carried out in the presence of a hydroxy-aromatic solvent (e.g., mixtures of phenols, alkyl phenols and methoxy alkyl phenols deriving from the hydrogenolysis of lignin carried out batchwise), said liquid phase can be directly subjected to hydrotreating.

Part of the depolymerized lignin deriving from said hydrogenolysis carried out batchwise can be optionally sent to the hydrogenolysis reactor (e.g., to the above autoclave), as hydrogenolysis solvent.

Said solid phase, comprising the catalyst and optionally part of the depolymerized lignin, can be subjected to extraction in the presence of at least one low-boiling solvent, having a boiling point lower than or equal to 120° C. such as, for example, acetone, methanol, ethanol, isopropanol, methyl acetate, ethyl acetate, methyl-ethyl ketone, preferably acetone, capable of dissolving the optional depolymerized lignin present in said solid phase, substantially leaving the catalyst as solid residue.

After extraction, the catalyst can be recovered by means of techniques known in the art, for example, by filtration or decanting, whereas the solvent/depolymerized lignin solution can be subjected to evaporation to recover the solvent which can be recycled to said extraction, and the depolymerized lignin which can be directly subjected to hydrotreating. The depolymerized lignin recovered after said evaporation is preferably joined to the depolymerized lignin obtained by hydrogenolysis carried out batchwise, in the presence of the low-boiling solvent, or in the presence of the hydroxy-aromatic solvent, before being subjected to hydrotreating.

The catalyst recovered as described above can be optionally dried in an oven at 110° C. and subsequently subjected to calcination, at a temperature ranging from 500° C. to 550° C., in order to determine the residue and to regenerate and recover the catalyst which can be subsequently recycled to said hydrogenolysis.

BRIEF DESCRIPTION OF THE DRAWINGS

FIG. 1 shows the gas chromatography/mass spectrometry (GC-MS) of the depolymerized lignin obtained by hydrogenolysis carried out batchwise, operating as described in Example 9 reported below in Table 1, where, in the abscissa is reported the analysis time and in the ordinate is reported the abundance of the various compounds present. The gas chromatography/mass spectrometry (GC-MS) was carried out using an Agilent gas chromatograph mod. 7890 equipped with a Mass Spectrometry Detector MSD 5975C. As can be seen in FIG. 1, the depolymerized lignin obtained by operating as described in Example 9 reported below in Table 1, comprises phenols, alkyl phenols and methoxy alkyl phenols.

Figure 1:
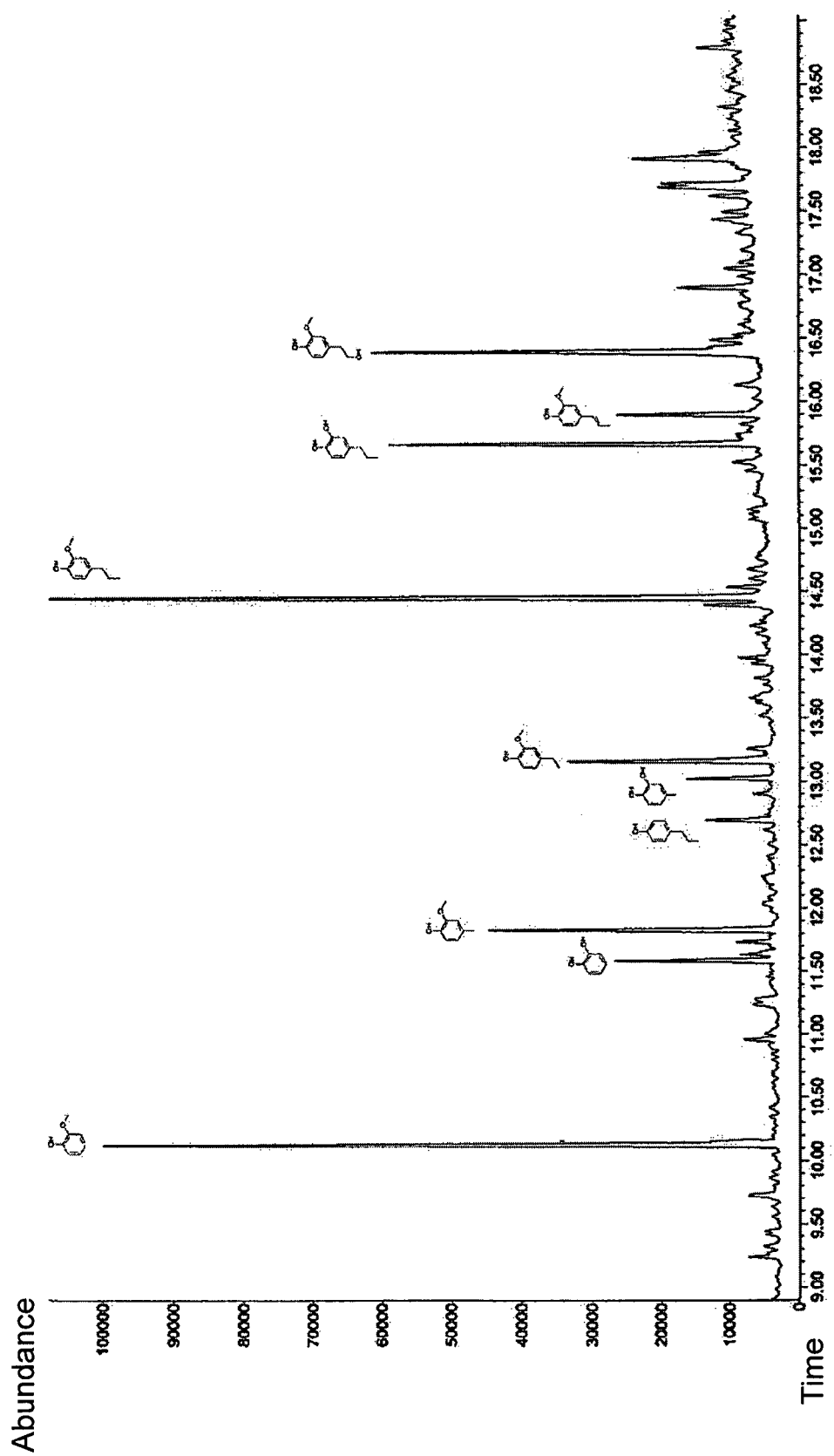
FIG. 1 shows the gas chromatography/mass spectrometry (GC-MS) of the depolymerized lignin obtained by hydrogenolysis carried out batchwise as described in Example 9 and reported in Table 1.

When said hydrogenolysis is carried out in continuous, it can be carried out in one or more catalytic reactors in series, having a fixed bed, or a fluid bed, being stirred or recirculated, or containing the catalyst in dispersion. Said hydrogenolysis carried out in continuous is preferably carried out in one or more fixed bed catalytic reactors in series.

According to a preferred embodiment of the present invention, said hydrogenolysis carried out in continuous can be carried out in the presence of a solvent.

In order to obtain a fluid mixture, the lignin and the hydrogenolysis solvent can be mixed before being sent to said one or more catalytic reactors. In this respect, when said hydrogenolysis is carried out in continuous, said lignin and said solvent can be sent to a mixer, operating at a temperature ranging from 50° C. to 150° C., preferably ranging from 80° C. to 120° C., for a time ranging from 10 minutes to 2 hours, preferably ranging from 15 minutes to 1 hour, before being sent to said one or more catalytic reactors.

According to a preferred embodiment of the present invention, said solvent can have a boiling point higher than or equal to 150° C., preferably ranging from 170° C. to 350° C., and can be selected from the hydroxy-aromatic solvents reported above. Said solvent is preferably selected from phenols, alkyl phenols and methoxy alkyl phenols deriving from the hydrogenolysis of lignin carried out in continuous, or batchwise.

It should be pointed out that when said hydrogenolysis is carried out in continuous, the ratio between lignin and solvent in the hydrogenolysis reactor is as high as possible, with the only limit that the lignin fed to the hydrogenolysis reactor is well dissolved, at the feeding temperature, in said solvent.

According to a preferred embodiment of the present invention, said hydrogenolysis carried out in continuous can be carried out operating at a Liquid Hourly Space Velocity (LHSV), i.e. a ratio between the volume of lignin, or between the volume of the lignin/solvent mixture, fed in one hour and the volume of catalyst, said ratio being measured in hours$^{-1}$, ranging from 0.2 hours$^{-1}$ to 6 hours$^{-1}$, preferably ranging from 0.25 hours$^{-1}$ to 3 hours$^{-1}$.

According to a preferred embodiment of the present invention, said hydrogenolysis carried out in continuous can be carried out at a partial hydrogen pressure ranging from 1 MPa to 20 MPa, preferably ranging from 3 MPa to 15 MPa.

When said hydrogenolysis is carried out in continuous, in order to obtain said partial hydrogen pressure, the hydrogen can be fed in excess, preferably in a volumetric ratio of 3,000 volumes of gaseous hydrogen measured under normal conditions (0° C., 100 kPa), per volume of lignin, or per volume of lignin/solvent mixture, fed, more preferably in a volumetric ratio ranging from 500 volumes of gaseous hydrogen to 2,000 volumes of gaseous hydrogen measured under normal conditions (0° C., 100 kPa), per volume of lignin, or per volume of lignin/solvent mixture, fed.

At the end of said hydrogenolysis carried out in continuous, a mixture comprising a liquid phase and a gas phase is obtained. The gas phase can be separated from the liquid phase by means of techniques known in the art, for example, by depressurization.

The gas phase obtained from the above separation can be subjected to purification in order to recover the hydrogen which can be recycled to said hydrogenolysis carried out in continuous.

Said liquid phase which comprises depolymerized lignin can be subjected directly to hydrotreating.

Part of the depolymerized lignin obtained from said hydrogenolysis carried out in continuous can be optionally sent to one or more catalytic reactors, as hydrogenolysis solvent.

It should be pointed out that said hydrogenolysis, whether it be carried out batchwise or in continuous, allows a high conversion of lignin to depolymerized lignin to be obtained, i.e. a conversion higher than or equal to 95% by weight, preferably higher than or equal to 99% by weight, with respect to the total weight of the starting lignin.

It should also be pointed out that said hydrogenolysis, whether it be carried out batchwise or in continuous, causes a partial deoxygenation of the starting lignin, equal to at least 10%, preferably higher than or equal to 15%, which is calculated as percentage ratio between the difference in weight percentages of the oxygen content of the starting lignin and that obtained after hydrogenolysis, divided by the weight percentage of the oxygen content of the starting lignin.

According to a preferred embodiment of the present invention, said hydrotreating can be carried out in a single step or in multisteps, preferably in a single step.

According to a preferred embodiment of the present invention, said hydrotreating can be carried out in the presence of at least one hydrotreating catalyst.

According to a preferred embodiment of the present invention, said hydrotreating catalyst can be selected from supported catalysts having formula (III), (V), (VI), (VII), or (VIII):

$$M^2/SiO_2 \quad \text{(III)},$$

$$M^3M/Al_2O_3 \quad \text{(V)},$$

$$M^3M/SiO_2\text{—}Al_2O_3 \quad \text{(VI)},$$

$$M^3MP/Al_2O_3 \quad \text{(VII)},$$

$$M^3MP/SiO_2\text{—}Al_2O_3 \quad \text{(VIII)},$$

wherein M is a metal selected from molybdenum, tungsten, $M^2$ is nickel, $M^3$ is a metal selected from cobalt, nickel, and P is phosphorous.

In addition to the carriers reported in the above formulae (III), (V), (VI), (VII) and (VIII), i.e. silica in the case of hydrotreating catalysts having formula (III), alumina in the case of hydrotreating catalysts having formula (V) and (VII), mixed silica-alumina oxides in the case of hydrotreating catalysts having formula (VI) and (VIII), other carriers can be used such as, for example, aluminium silicates, amorphous or crystalline, materials based on spinels having the formula $AB_2O_4$ wherein A is a bivalent metal ion such as, for example, bivalent iron, magnesium, zinc, manganese, nickel, whereas B is a trivalent metal ion such as, for example, aluminium, trivalent iron, chromium. Carriers based on mixtures of the inorganic materials reported above, well-known in the state of the art, can be equally used.

Preferably, in the above hydrotreating catalysts having formulae (V), (VI), (VII), or (VIII), the metal content (M) can range from 2% by weight to 20% by weight, more preferably from 6% by weight to 14% by weight, with respect to the total weight of the hydrotreating catalyst, and the metal content ($M^3$) can range from 0.5% by weight to 10% by weight, more preferably from 2% by weight to 6% by weight, with respect to the total weight of the hydrotreating catalyst. Preferably, in the above hydrotreating catalysts having formula (VII), or (VIII), the phosphorous content (P) can range from 0.5% by weight to 8% by weight, more preferably from 2% by weight to 5% by weight, with respect to the total weight of the hydrotreating catalyst. Preferably, in the above hydrotreating catalysts having formula (III), the metal content ($M^2$) can range from 1% by weight to 65% by weight, with respect to the total weight of the hydrotreating catalyst.

According to a preferred embodiment of the present invention, in the above hydrotreating catalysts having formulae (III), (V), (VI), (VII), or (VIII), the metals deposited on the carriers (i.e. alumina, silica, mixed silica-alumina oxides) can be used in their sulphidated form rather than in the form of oxides. The transformation of the metal oxides into the respective sulphides can be carried out by any means known in the art suitable for the purpose such as, for example, by means of sulphidation with hydrogen sulphide ($H_2S$), or with dimethyldisulphide. Said sulphidation can be carried out in a separate step before the use of said catalyst in the hydrotreating of the depolymerized lignin, or during the hydrotreating of the depolymerized lignin.

If the sulphidation is carried out in a separate step, the sulphidation temperature is preferably that envisaged for the subsequently hydrotreating, or slightly lower.

If the sulphidation is carried out in a separate step using dimethyldisulphide (DMDS), said sulphidation can be carried out for a time higher than or equal to 5 hours, operating in the presence of a stoichiometric excess of dimethyldisulphide (DMDS), preferably with a ratio of dimethyldisulphide (DMDS) moles/mole of metal deposited on the carrier ranging from 5 to 10, in the presence of a partial hydrogen pressure ranging from 4 MPa to 8 MPa.

If the sulphidation is carried out in a separate step using hydrogen sulphide ($H_2S$), said sulphidation can be carried out at a temperature of about 400° C., by putting the catalyst in contact with a stream of hydrogen which contains about 5% by volume of hydrogen sulphide ($H_2S$), in a tubular reactor, for at least 3 hours. Sulphidation techniques which can be well used for transforming the catalysts of the present invention into the corresponding sulphides are described, for example, in "Petroleum Refining: Technology and Economics" (1994), J. H. Gary et al., M. Dekker Ed., 3rd edition, page 465.

If the sulphidation is carried out during the hydrotreating, hydrogen sulphide ($H_2S$) can be used, which can be injected into the reactor in which the hydrotreating is carried out (e.g., in an autoclave, or into a tubular reactor) by means of the hydrogen stream used in the above hydrotreating: for this purpose, about 5% by volume of hydrogen sulphide ($H_2S$) is added to said hydrogen stream.

Hydrotreating catalysts having formula (III), (V), (VI), (VII), or (VIII), of the type described above, are commercially available and are produced, for example, by: Degussa, Engelhard (now Basf), UOP, Kata Leuna, Axens.

Alternatively, hydrotreating catalysts having formula (III), (V), (VI), (VII), or (VIII), of the type described above, can be produced according to processes known in the art as reported for example in Examples 1-3 which follow.

For the purposes of the present invention, said hydrotreating can be carried out batchwise, or in continuous, preferably in continuous.

If the hydrotreating is carried out batchwise, for example in a stirred and heated autoclave, said hydrotreating catalyst can be used in an amount ranging from 0.1% by weight to 20% by weight, preferably from 1% by weight to 10% by weight, with respect to the total weight of the depolymerized lignin.

According to a preferred embodiment of the present invention, said hydrotreating carried out batchwise, can be carried out in the presence of a solvent selected from:

linear, branched or cyclic $C_{10}$-$C_{12}$ hydrocarbons, such as, for example: decane; dodecane; decahydronaphthalene (decalin); tetrahydronaphthalene (tetralin); dihydronaphthalene; or mixtures thereof; said hydrocarbons having a boiling point ranging from 170° C. to 210° C., preferably ranging from 180° C. to 200° C.;

hydroxy-aromatic solvents having a boiling point higher than or equal to 150° C., preferably ranging from 170° C. to 350° C., such as, for example: phenol; cresol; 2-methoxy-4-ethyl-phenol; 2-methoxy-4-(2-propyl)-phenol; mixtures of phenols, alkyl phenols and methoxy alkyl phenols deriving from the hydrogenolysis of lignin carried out batchwise, or in continuous; or mixtures thereof.

Mixtures of phenols, alkyl phenols and methoxy alkyl phenols deriving from the hydrogenolysis of lignin carried out batchwise, or in continuous, are preferred.

According to a preferred embodiment of the present invention, said solvent can be used in such a quantity as to have a weight ratio solvent/depolymerized lignin lower than or equal to 15/1, preferably ranging from 10/1 to 0.5/1.

According to a preferred embodiment of the present invention, said hydrotreating carried out batchwise, can be carried out at a partial hydrogen pressure ranging from 1 MPa to 25 MPa, preferably from 3 MPa to 20 MPa.

According to a preferred embodiment of the present invention, said hydrotreating carried out batchwise, can be carried out at a temperature ranging from 300° C. to 500° C., preferably ranging from 380° C. to 420° C.

According to a preferred embodiment of the present invention, said hydrotreating carried out batchwise, can be carried out for a time ranging from 6 minutes to hours, preferably ranging from 12 minutes to 5 hours.

At the end of said hydrotreating carried out batchwise, a mixture is obtained, comprising at least a liquid phase, a solid phase and a gas phase. The gas phase can be separated from the liquid phase and from the solid phase by means of techniques known in the art, for example by depressurization of the autoclave in which said hydrotreating is carried out batchwise. Said liquid phase can be separated from said solid phase by techniques known in the art, for example by filtration or decanting.

Said mixture, separated from the gas phase and the solid phase, comprises a first liquid phase comprising a mixture of liquid hydrocarbons and a second liquid phase comprising the water produced during said hydrotreating carried out batchwise. Said first liquid phase and said second liquid phase can be separated by means of techniques known in the art, for example, by means of demixing. The mixture of liquid hydrocarbons thus obtained can be subjected to fractionation, for example, by means of a fractionation column, obtaining:

when the solvent of the hydrotreating carried out batchwise is selected from hydrocarbons having a boiling point ranging from 170° C. to 210° C. described above: (i) a fraction comprising liquid hydrocarbons having a boiling point lower than 200° C., more specifically lower than the boiling point of said solvent; (ii) a fraction comprising liquid hydrocarbons having a boiling point higher than or equal to 200° C.; (iii) a fraction comprising said solvent;

when the solvent of the hydrotreating carried out batchwise is selected from hydroxy-aromatic solvents having a boiling point higher than or equal to 150° C. described above: (i) a fraction comprising liquid hydrocarbons having a boiling point lower than 200° C.; (ii) a fraction comprising liquid hydrocarbons having a boiling point higher than or equal to 200° C.

Said fraction (i) essentially comprises linear or branched alkyl hydrocarbons, alkyl-cyclo-alkanes and alkylbenzenes having from 5 to 9 carbon atoms.

Figure 2:
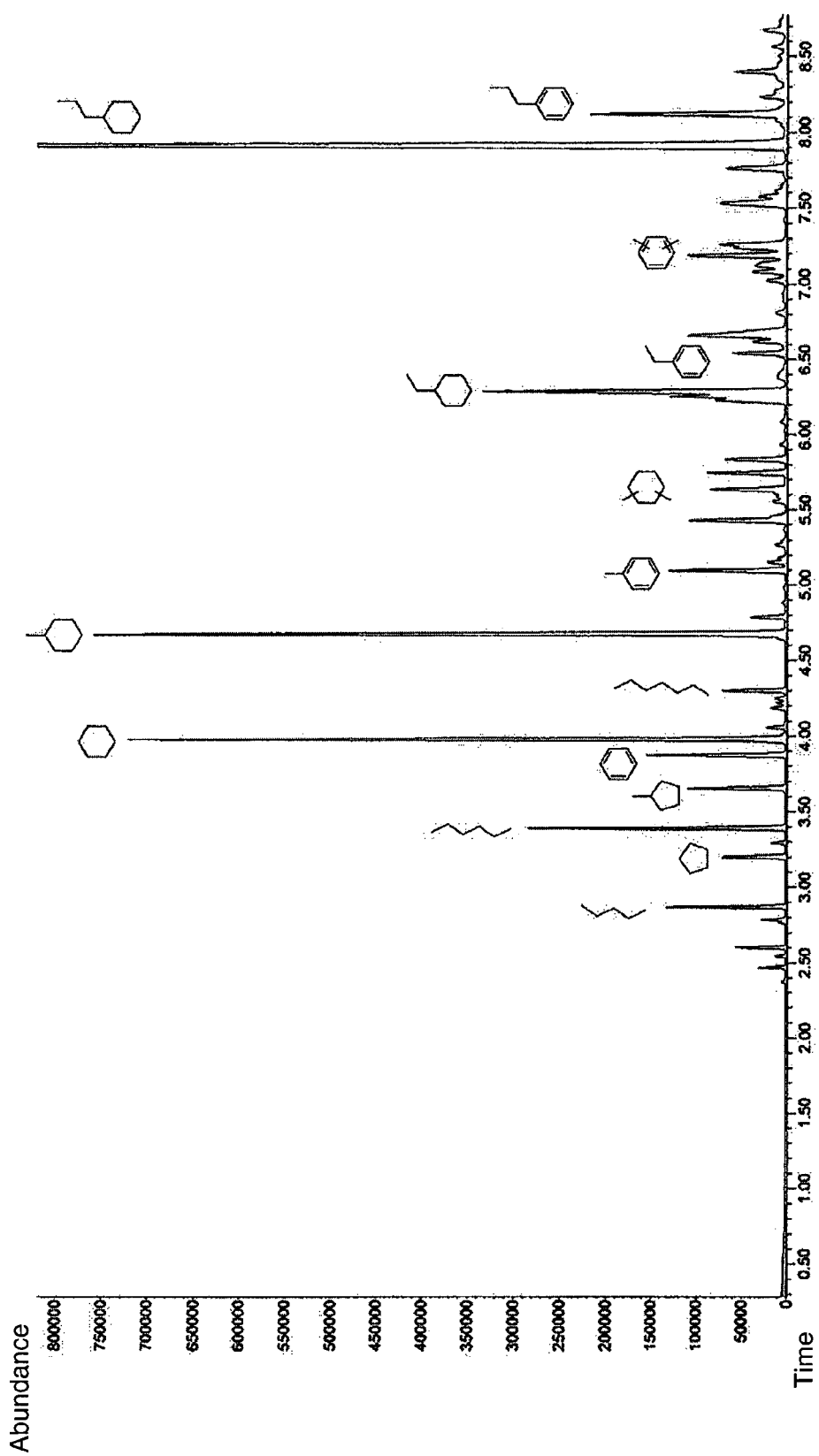
FIG. 2 shows the gas chromatography/mass spectrometry (GC-MS) of a typical hydrotreated fraction (i) obtained as described in Example 16 and reported in Table 3.

FIG. 2 shows a gas chromatography/mass spectrometry (GC-MS) typical of said fraction (i), obtained as described in Example 16 reported below in Table 3, where, in the abscissa is reported the analysis time and in the ordinate is reported the abundance of the various compounds present. The gas chromatography/mass spectrometry (GC-MS) was carried out using an Agilent gas chromatograph mod. 7890 equipped with a Mass Spectrometry Detector MSD 5975C.

Said solid phase comprising the catalyst and optionally an insoluble polar fraction, can be subjected to extraction in the presence of at least one low-boiling solvent having a boiling point lower than or equal to 120° C. such as, for example, acetone, methanol, ethanol, isopropanol, methyl acetate, ethyl acetate, methyl-ethyl ketone, preferably acetone, capable of dissolving the optional insoluble polar fraction present in said solid phase, leaving substantially the catalyst as solid residue.

After extraction, the catalyst can be recovered by means of techniques known in the art, for example by filtration or decanting, whereas the solution of solvent/insoluble polar fraction can be subjected to evaporation in order to recover the solvent which can be recycled to said extraction, and the insoluble polar fraction which can be recycled to said hydrotreating carried out batchwise.

The catalyst recovered as described above, can be optionally dried in an oven at 110° C. and subsequently subjected to calcination, at a temperature ranging from 500° C. to 550° C., in order to determine the residue and to regenerate and recover the catalyst which can be subsequently recycled to said hydrotreating carried out batchwise.

When said hydrotreating is carried out in continuous, it can be carried out in one or more catalytic reactors in series, having a fixed bed, or a fluid bed, being stirred or recirculated, or containing the catalyst in dispersion. Said hydrotreating carried out in continuous is preferably carried out in one or more fixed bed catalytic reactors in series.

According to a preferred embodiment of the present invention, said hydrotreating carried out in continuous can be carried out without a solvent.

It should be pointed out that said hydrotreating carried out in continuous is optionally carried out in the presence of a solvent which can be selected from hydroxy-aromatic solvents having a boiling point higher than or equal to 150° C., preferably ranging from 170° C. to 350° C., such as, for example: phenol; cresol; 2-methoxy-4-ethyl-phenol; 2-methoxy-4-(2-propyl)-phenol; mixtures of phenols, alkyl phenols and methoxy alkyl phenols deriving from the hydrogenolysis of lignin carried out batchwise, or in continuous; or mixtures thereof. Mixtures of phenols, alkyl phenols and methoxy alkyl phenols deriving from the hydrogenolysis of lignin carried out batchwise, or in continuous, are preferred.

According to a preferred embodiment of the present invention, said hydrotreating carried out in continuous can be carried out at a Liquid Hourly Space Velocity (LHSV), i.e. at a ratio between the volume of the depolymerized lignin, or between the volume of the depolymerized lignin/solvent mixture, fed in one hour, and the volume of the catalyst, said ratio being measured in hours$^{-1}$, ranging from 0.2 hours$^{-1}$ to 6 hours$^{-1}$, preferably ranging from 0.25 hours$^{-1}$ to 3 hours$^{-1}$.

According to a preferred embodiment of the present invention, said hydrotreating carried out in continuous can be carried out at a partial hydrogen pressure ranging from 1 MPa to 25 MPa, preferably ranging from 3 MPa to 20 MPa.

When said hydrotreating is carried out in continuous, in order to obtain said partial hydrogen pressure, the hydrogen can be fed in excess, preferably in a volumetric ratio of 3,000 volumes of gaseous hydrogen measured under normal conditions (0° C., 100 kPa), per volume of depolymerized lignin, or per volume of depolymerized lignin/solvent mixture, fed, more preferably in a volumetric ratio ranging from 500 volumes of gaseous hydrogen to 2,000 volumes of gaseous hydrogen measured under normal conditions (0° C., 100 kPa), per volume of depolymerized lignin, or per volume of depolymerized lignin/solvent mixture, fed.

According to a preferred embodiment of the present invention, said hydrotreating carried out in continuous can be carried out at a temperature ranging from 300° C. to 500° C., preferably ranging from 380° C. to 420° C.

At the end of said hydrotreating carried out in continuous, a mixture comprising at least a liquid phase and a gas phase is obtained. The gas phase can be separated from the liquid phase by means of techniques known in the art, for example, by means of depressurization.

The gas phase obtained from the above separation can be subjected to purification in order to recover the hydrogen which can be recycled to said hydrotreating carried out in continuous.

Said mixture, separated from the gas phase, comprises a first liquid phase comprising a mixture of liquid hydrocarbons and a second liquid phase comprising the water produced during said hydrotreating. Said first liquid phase and said second liquid phase can be separated by means of techniques known in the art, for example by demixing. The mixture of liquid hydrocarbons thus obtained can be subjected to fractionation, for example, by means of a fractionation column, obtaining: (i) a fraction comprising liquid hydrocarbons having a boiling point lower than 200° C.; (ii) a fraction comprising liquid hydrocarbons having a boiling point higher than or equal to 200° C.

It should be pointed out that when said hydrotreating is carried out batchwise and also when said hydrotreating is carried out in continuous, the following fractions can be obtained:
  a fraction (i) comprising liquid hydrocarbons, having as reported above, a boiling point lower than 200° C., or lower than the boiling point of the solvent used for the hydrotreating carried out batchwise, which can be advantageously used as such as biofuels, or for the production of reformulated gasolines;
  a fraction (ii) comprising liquid hydrocarbons having a boiling point higher than or equal to 200° C., characterized by an oxygen content lower than 2% by weight, preferably lower than 1% by weight, which can be fed to the hydrocracking section of a refinery for the production of further fuel (gasolines or gas oils).

It should also be pointed out that said hydrotreating, when carried out both batchwise and in continuous, allows a yield to liquid hydrocarbons to be obtained, higher than or equal to 45% by weight, preferably higher than or equal to 50% by weight, with respect to the total weight of depolymerized lignin subjected to hydrotreating.

Figure 3:
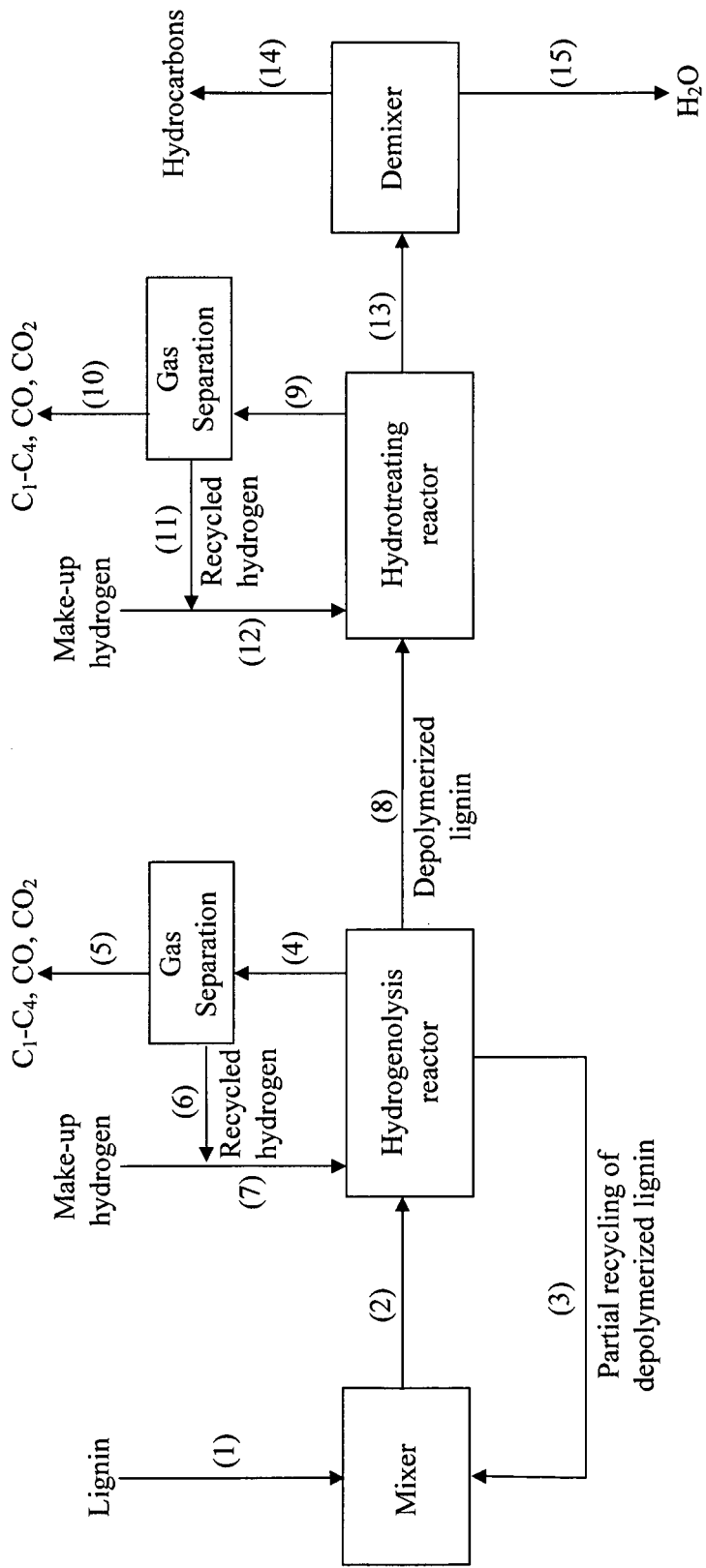
FIG. 3 shows a typical embodiment of a continuous process of the present invention.

The present invention will now be illustrated in greater detail through an illustrative embodiment with reference to FIG. 3 provided hereunder.

In particular, FIG. 3 shows a typical embodiment of the process object of the present invention, carried out in continuous.

With reference to FIG. 3, the lignin (1) and part of the depolymerized lignin (3), are sent to a heated mixer (e.g., heated to 100° C.). The fluid mixture (2) obtained is sent to the hydrogenolysis reactor, for example, a fixed bed hydrogenolysis catalytic reactor. Hydrogen in excess [i.e. make-up hydrogen (7) and recycled hydrogen (6)] is also sent to said hydrogenolysis reactor.

At the end of the hydrogenolysis, a mixture comprising a liquid phase and a gas phase is obtained. The gas phase (4) is separated from the liquid phase (8) by means of depressurization. As reported above, part of the depolymerized lignin (3) (e.g., the mixture of phenols, alkyl phenols and methoxy alkyl phenols deriving from said hydrogenolysis of lignin), is sent to the mixer, whereas the remaining part, i.e. the liquid phase (8), is sent to the hydrotreating catalytic reactor.

Said gas phase (4) is sent to a gas separator in order to recover the hydrogen (6) and to separate it from the off-gases [i.e. $C_1$-$C_4$ hydrocarbons, carbon monoxide (CO) and carbon dioxide ($CO_2$) (5)]. Said hydrogen (6), after being joined with the make-up hydrogen (7), is sent to the above hydrogenolysis catalytic reactor.

The depolymerized lignin (8) and the excess hydrogen [i.e. make-up hydrogen (12) and recycled hydrogen (11)] are sent to the hydrotreating catalytic reactor, for example a fixed bed catalytic reactor.

At the end of the hydrotreating, a mixture comprising a liquid phase and a gas phase is obtained. The gas phase (9) is separated from the liquid phase (13) by means of depressurization.

Said gas phase (9) is sent to a gas separator in order to recover the hydrogen (11) and to separate it from the off-gases [i.e. $C_1$-$C_4$ hydrocarbons, carbon monoxide (CO) and carbon dioxide ($CO_2$) (10)]. Said hydrogen (11), after being joined with the make-up hydrogen (12), is sent to the above hydrotreating catalytic reactor.

Said liquid phase (13) is sent to a demixer to separate the reaction water (15) and a mixture of liquid hydrocarbons (14). Said mixture of liquid hydrocarbons (14) is subjected to fractionation by means of a fractionation column (not represented in FIG. 3), obtaining: (i) a fraction comprising liquid hydrocarbons having a boiling point lower than 200° C.; (ii) a fraction comprising liquid hydrocarbons having a boiling point higher than or equal to 200° C.

Some illustrative and non-limiting examples are provided hereunder for a better understanding of the present invention and for its embodiment.

EXAMPLE 1

Preparation of the Catalyst Ni(4%)Mo(10%)/$Al_2O_3$ used in the following Examples 14 and 15

150 g of pseudobohemite (V-250 of UOP) were added to 150 g of a solution of acetic acid at 3%. The whole mixture was stirred for 20 minutes and a further 1,350 g of the acetic acid solution at 3% was subsequently added. The suspension obtained was heated, under stirring, to 60° C., for 90 minutes. The mixture obtained was dried, by heating, under stirring, obtaining a solid product. The solid product obtained was dried at 120° C., for 14 hours, and was then calcined at 500° C., for 4 hours. The solid product thus obtained was ground and granulated into the 20-40 mesh fraction.

61 g of the granulated product were impregnated with a solution comprising 5.08 g of nickel nitrate hexahydrate and 4.64 g of ammonium molybdate dissolved in 56 g of water and the whole mixture was left to rest for 90 minutes and was subsequently dried at 140° C. Subsequently, the product obtained was impregnated again and dried a further two times, operating under the same conditions previously described (i.e. 90 minutes and 140° C.). The dried product was then calcined at 500° C., for 4 hours, obtaining a catalyst having a nickel content equal to 4% by weight with respect to the total weight of the catalyst and a molybdenum content equal to 10% by weight with respect to the total weight of the catalyst.

EXAMPLE 2

Preparation of the Catalyst Co(4%)Mo(10%)/$Al_2O_3$ 100 g of pseudobohemite (V-250 of UOP) were added to 100 g of a solution of acetic acid at 3%. The whole mixture was stirred for 10 minutes and a further 900 g of the acetic acid solution at 3% were subsequently added. The suspension obtained was heated, under stirring, to 60° C., for 90 minutes.

The mixture obtained was dried, by heating, under stirring, obtaining a solid product. The solid product obtained was dried at 130° C., for 14 hours, and was then calcined at 500° C., for 4 hours. The solid product thus obtained was ground and granulated into the 20-40 mesh fraction.

12.5 g of the granulated product were impregnated with a solution comprising 1.04 g of cobalt nitrate hexahydrate and 0.95 g of ammonium molybdate dissolved in 11.5 g of water and the whole mixture was left to rest for 90 minutes and was subsequently dried at 140° C. Subsequently, the product obtained was impregnated again and dried a further two times, operating under the same conditions previously described (i.e. 90 minutes and 140° C.). The dried product was then calcined at 500° C., for 4 hours, obtaining a catalyst having a cobalt content equal to 4% by weight with respect to the total weight of the catalyst and a molybdenum content equal to 10% by weight with respect to the total weight of the catalyst.

EXAMPLE 3

Preparation of the Sulphided Catalysts Used in the Following Examples 5, 15, 16 and 17

1 g of the catalyst prepared as described in Example 1 or Example 2 provided above, or of the catalyst UF210 of UOP, 100 g of decalin and 1 ml of dimethyl disulphide, were introduced into a 0.5 l stirred autoclave, made of Hastelloy C. The autoclave was pressurized with hydrogen to about 3 MPa and was heated to 330° C., for about 4 hours. The autoclave was then cooled and the excess gas was discharged obtaining the sulphided catalyst which was preserved, submersed in decalin, in an inert atmosphere, until use.

EXAMPLES 4-13

Hydrogenolysis of Lignin

The lignin used in Examples 4 to 13 is of the Acetosolv type for Examples 4, 5 and 6 (comparative) and for Examples 9, 10, 11 and 13 (invention), of the Organosolv type for Examples 7 and 8 (invention) and of the Kraft type for Example 12 (invention).

The lignin of the Acetosolv type was obtained from a mixture of fir/pine wood, operating as described in the article of X. Pan et al. "Acetic acid pulping of wheat straw under atmospheric pressure", published in "Journal of Wood Science" (1999), Vol. 45 (4), pages 319-325. The lignins of the Organosolv and Kraft types used are commercial products from the Aldrich catalogue cod. 371017 (batch 10228TC) and cod. 471003 (batch 09724CE), respectively.

The lignins of the Acetosolv type, of the Organosolv type and of the Kraft type used have the following elemental composition:
C % 67.1; H % 5.3; N % 0.1; S % 0.0; O % 27.6 (lignin of the Acetosolv type);
C % 66.7; H % 5.3; N % 0.2; S % 0.0; O % 28.9 (lignin of the Organosolv type);
C % 63.3; H % 6.9; N % 0.2; S % 4.3; O % 25.4; inorganic ashes 17.5% (lignin of the Kraft type).

10 g of lignin were added to a stirred 0.5 l Hastelloy C autoclave containing 100 g of a solvent (the type of solvent is reported in Table 1) and a catalyst (the type of catalyst is reported in Table 1). The autoclave was closed and pressurized with about 5 MPa of hydrogen at room temperature (25° C.).

The autoclave was then stirred at 600 rpm and heated to the temperature and for the time reported in Table 1. At the end, the autoclave was left to cool to room temperature (25° C.), again under stirring, and the gas released was measured by means of a liters counter and analyzed by means of gas chromatography in order to determine the content of $C_1$-$C_4$ hydrocarbons and carbon monoxide and carbon dioxide.

The mixture obtained, comprising a first liquid phase and a solid phase, was filtered obtaining a first liquid phase comprising part of the depolymerized lignin and a solid phase comprising the catalyst and the remaining part of the depolymerized lignin.

Said liquid phase was subjected to evaporation in order to recover the depolymerized lignin (fraction 1) and the solvent which can be re-used for the hydrogenolysis of lignin.

Said solid phase was subjected to extraction with 200 ml of acetone obtaining a solution comprising depolymerized lignin and catalyst. Said solution was filtered so as to obtain a solid residue comprising the catalyst and a second liquid phase comprising depolymerized lignin and acetone.

The depolymerized lignin was recovered by evaporation of the acetone (fraction 2). Said fraction 2 and said fraction 1 were joined and sent to the hydrotreating reactor.

The above solid residue comprising the catalyst was dried in an oven, at 110° C., for 24 hours and subsequently calcined at about 500° C., for 6 hours, in the air. The difference in weight between the dried catalyst and the calcined catalyst in relation to the starting lignin provides the residue reported in Table 1. The calcined catalyst can be re-used for the hydrogenolysis of lignin.

As reported above, FIG. 1 indicates a gas chromatography/mass spectrometry (GC-MS) typical of the depolymerized lignin, obtained operating as described in Example 9 reported in Table 1, where, in the abscissa is reported the analysis time and in the ordinate is reported the abundance of the various compounds present. The gas chromatography/mass spectrometry (GC-MS) was carried out using an Agilent gas chromatograph mod. 7890 equipped with a Mass Spectrometry Detector MSD 5975C. As can be seen in FIG. 1, the depolymerized lignin obtained as described above comprises phenols, alkyl phenols and methoxy alkyl phenols.

The depolymerized lignin obtained after joining said fraction 1 and said fraction 2 was weighed and subjected to elemental analysis by means of a Thermo Scientific Flash CHNS-O analyzer, in order to determine its content of carbon, hydrogen, nitrogen, sulphur and, by difference, oxygen: the data obtained are reported in Table 2. From the data reported in Table 2, it can be deduced that during the hydrogenolysis, a partial deoxygenation of lignin is obtained.

From the data reported in Table 1, it can also be deduced that the lignin of the Acetosolv type and the lignin of the Organosolv type, after hydrogenolysis, are completely soluble in acetone, the solvent used for recovering them (Examples 7-11 and 13), whereas, for the lignin of the Kraft type, an insoluble residue equal to 4% by weight with respect to the total weight of the starting lignin (Example 12) can be observed. It can also be deduced that the presence of the catalyst is essential: Example 4 carried out in the absence of the catalyst, in fact, shows a residue of lignin (33% by weight with respect to the total weight of the starting lignin) not soluble in acetone and therefore not depolymerized. Furthermore, it can also be deduced that by operating in a single step, at a higher temperature, as in Example 5 and in Example 6, there is a lignin residue (25% by weight and 13% by weight with respect to the total weight of the starting lignin, respectively) not soluble in acetone and therefore not depolymerized.

EXAMPLES 14-19

Hydrotreating of the Depolymerized Lignin 10 g of depolymerized lignin obtained as described in Example 9 reported above, were added to a stirred 0.5 l Hastelloy C autoclave containing 100 g of decalin and a catalyst (the type of catalyst is reported in Table 3), in the quantities reported in Table 3. The autoclave was closed and pressurized with about 5 MPa of hydrogen at room temperature (25° C.).

The autoclave was then heated to the temperature reported in Table 3 and was left at this temperature for 6 hours. At the end, the autoclave was left to cool to room temperature (25° C.) and the gas released was measured with a liters counter and analyzed by means of gas chromatography in order to determine the content of $C_1$-$C_4$ hydrocarbons and carbon monoxide and carbon dioxide.

The mixture obtained includes a first liquid phase comprising a mixture of liquid hydrocarbons and decalin used as solvent, a second liquid phase comprising the water produced during said process (i.e. reaction water), and a solid phase comprising the catalyst. Said first liquid phase and said second liquid phase were sent to a demixer obtaining reaction water and a mixture of liquid hydrocarbons comprising: (i) a fraction comprising liquid hydrocarbons having a boiling point lower than 180° C.; (ii) a fraction comprising liquid hydrocarbons having a boiling point higher than or equal to 200° C.; (ii) a fraction comprising decalin.

An aliquot of said mixture of liquid hydrocarbons was subjected to gas chromatography to determine the liquid hydrocarbons having a boiling point (b.p.) lower than 180° C. and the values obtained are reported in Table 3. The liquid hydrocarbons having a boiling point (b.p.) higher than 200° C. were determined by ponderal weight, by distilling-off at reduced pressure the decalin (1 mm/Hg, 100° C.), weighing the residue: the values obtained are reported in Table 3.

The residue of liquid hydrocarbons obtained after evaporation of the decalin was subjected to elemental analysis by means of a Thermo Scientific Flash CHNS-O analyzer in order to determine its content of carbon, hydrogen, nitrogen, sulphur and, by difference, oxygen: the data obtained are reported in Table 4. From the data reported in Table 4, it can be deduced that during the hydrotreating, the deoxygenation of the depolymerized lignin is obtained.

The liquid hydrocarbons having a boiling point lower than 180° C. essentially comprise linear or branched alkyl hydrocarbons, alkyl-cyclo-alkanes and alkylbenzenes having from 5 to 9 carbon atoms. As reported above, FIG. 2, indicates a gas chromatography/mass spectrometry (GC-MS) typical of said hydrocarbons, obtained as described in Example 13 reported in Table 3, where, in the abscissa is reported the analysis time and in the ordinate is reported the abundance of the various compounds present. The gas chromatography/mass spectrometry (GC-MS) was carried out using an Agilent gas chromatograph mod. 7890 equipped with a Mass Spectrometry Detector MSD 5975C. Said hydrocarbons are particularly suitable for the production of reformulated gasolines.

Said solid phase was subjected to extraction with acetone in order to separate the insoluble polar fraction comprising residual polar compounds, from the catalyst. These residual polar compounds are obtained by evaporation of the acetone, in particular, phenols, alkyl phenols and methoxy alkyl phenols, which were determined by weighing: the values obtained are reported in Table 3.

The solid filtration residue comprising the catalyst was dried in an oven at 110° C., for 24 hours and subsequently calcined at about 500° C., for 6 hours, in the air. The difference in weight between the dried catalyst and the calcined catalyst in relation to the starting lignin provides the residue reported in Table 3. The calcined catalyst can be re-used for the hydrotreating of the depolymerized lignin.

TABLE 1

| Ex. | Lignin | Solvent | Catalysed[d] | Temp. (° C.) | Time (h) | Residue (%)[c] | Depolymerised lignin (%)[c] | Gas ($C_1$-$C_4$, CO, $CO_2$) (%) |
|---|---|---|---|---|---|---|---|---|
| 4 | Acetosolv | Water | | 310 | 1 | 33 | 52 | 1.5 |
| 5 | Acetosolv | Decalin | Ni(4%)Mo(10%)/$Al_2O_3$[f] | 385 | 6 | 19 | 46[b] | 2 |
| 6 | Acetosolv | Decalin | Pd(5%)C (ESCAT 10-Engelhard) | 385 | 6 | 13 | 54[b] | 2 |
| 7 | Organosolv | Water | Pd(5%)C (ESCAT 10-Engelhard) | 310 | 1 | 0 | 87 | 0.8 |
| 8 | Organosolv | Water | Pd(5%)$Al_2O_3$ (ESCAT 14-Engelhard) | 310 | 1 | 0 | 81 | 0.8 |
| 9 | Acetosolv | Water | Pd(5%)$Al_2O_3$ (ESCAT 14-Engelhard) | 310 | 1 | 0 | 79 | 0.8 |
| 10 | Acetosolv | Methanol | Pd(5%)$Al_2O_3$ (ESCAT 14-Engelhard) | 310 | 1 | 0 | 78 | 2.8 |
| 11 | Acetosolv | Water | Ni(56%)$SiO_2$ (Ni-6458-Engelhard) | 310 | 1 | 0 | 81 | 0.8 |
| 12 | Kraft | Water | Ni(56%)$SiO_2$ (Ni-6458-Engelhard) | 310 | 1 | 4 | 48[e] | 1.8 |
| 13[a] | Acetosolv | Water | Ni(56%)$SiO_2$ (Ni-6458-Engelhard) | 310 | 3 | 0 | 73 | 1.1 |

[a]catalyst: 2.5% by weight with respect to the total weight of the starting lignin;
[b]mixture of hydrocarbons and phenols;
[c]% by weight with respect to the total weight of the starting lignin;
[d]in brackets the weight % of the metal with respect to the total weight of the catalyst and the trade-name of the catalyst;
[e]% by weight with respect to the total weight of the starting lignin including the inorganic ashes present therein;
[f]sulphided catalyst obtained as described in Example 3

Operative conditions:
catalyst: 10% by weight with respect to the total weight of the starting lignin;
partial hydrogen pressure, at room temperature (25° C.): 5 MPa;
solvent/lignin ratio: 10/1.

TABLE 2

Elemental analysis of the depolymerized lignins reported in Table 1

| Example | C (%) | H (%) | N (%) | S (%) | O (%) | Ashes (%) | Deoxygenation (%) |
|---|---|---|---|---|---|---|---|
| Acetosolv | 67.1 | 5.3 | 0.1 | 0 | 27.6 | — | — |
| Oragnosolv | 66.7 | 5.3 | 0.2 | 0 | 28.9 | — | — |
| Kraft | 63.3 | 6.9 | 0.2 | 4.3 | 25.4 | 17.5 | — |
| 7[b] | 69.4 | 6.4 | 0.1 | 0 | 24.2 | — | 16 |
| 8[b] | 71.6 | 6.3 | 0.2 | 0 | 22.1 | — | 24 |
| 9[a] | 74.6 | 5.7 | 0 | 0 | 19.6 | — | 29 |
| 10[a] | 69.4 | 6.8 | 0.1 | 0 | 23.6 | — | 15 |
| 11[a] | 72.7 | 6.9 | 0 | 0 | 20.3 | — | 26 |
| 12[c] | 75.8 | 7.5 | 0.1 | 0 | 16.7 | — | 34 |
| 13[a] | 74.4 | 6.8 | 0 | 0 | 8.8 | — | 37 |

[a]Acetosolv;
[b]Organosolv
[c]Kraft

TABLE 3

| Ex. | Catalyst[e] | Temperature | Residue (%)[b] | Polar fraction (%)[b] | Liquid hydrocarbons with b.p. <180° C. (%)[b] | Liquid hydrocarbons with b.p. ≥200° C. (%)[b] | Gas (C$_1$-C$_4$, CO, CO$_2$) (%)[b] |
|---|---|---|---|---|---|---|---|
| 14[a] | Ni(4%)Mo(10%)/Al$_2$O$_3$ | 385 | 0 | 5 | 31 | 27 | 2.0 |
| 15[f] | Ni(4%)Mo(10%)/Al$_2$O$_3$ | 385 | 0 | 3 | 27 | 20 | 2.0 |
| 16[f] | Co(4%)Mo(10%)/Al$_2$O$_3$ | 385 | 0 | 2 | 31 | 21 | 2.2 |
| 17[f] | UF210[c](UOP) | 385 | 0 | 2 | 38 | 18 | 2.3 |
| 18[a] | UF210[c](UOP) | 385 | 0 | 9 | 20 | 30 | 2.5 |
| 19[a1] | Ni-6458[c](Engelhard) | 400 | 0 | 10 | 23 | 43 | 1.5 |
| 20[a1] | HPC-60K[c] (Engelhard) | 400 | 0 | 5 | 29 | 38 | 1.0 |
| 21[a1] | HPC-50K[c] (Engelhard) | 400 | 0 | 5 | 21 | 42 | 1.0 |

[a]non-sulphided catalyst obtained as described in Example 1;
[a1]non-sulphided catalyst;
[b]% by weight with respect to the total weight of the starting depolymerized lignin;
[c]trade-name
[e]in brackets the weight % of the metal with respect to the total weight of the catalyst and the name of the catalyst producer;
[f]sulphided catalyst obtained as described in Example 3;

Operative conditions:
catalyst: 10% by weight with respect to the total weight of the starting depolymerized lignin;
solvent: decahydronaphthalene (decalin)
partial hydrogen pressure, at room temperature (25° C.): 5 MPa;
decalin/lignin ratio: 10/1;
temperature: 385° C.
time: 6 hrs

TABLE 4

Elemental analysis of the liquid hydrocarbons having b.p. ≥200° C. reported in table 3

| Example | C (%) | H (%) | N (%) | S (%) | O (%) |
|---|---|---|---|---|---|
| 14 | 88.1 | 8.9 | 0 | 0 | 3.0 |
| 15 | 89.9 | 10.4 | 0 | 0 | 0 |
| 16 | 92.3 | 9.4 | 0 | 0 | 0 |
| 17 | 91.3 | 9.4 | 0 | 0 | 0 |
| 18 | 87.4 | 8.6 | 0.1 | 0 | 4.0 |
| 19 | 85.2 | 9.5 | 0 | 0 | 5.3 |
| 20 | 89.0 | 8.0 | 0.1 | 0 | 2.9 |
| 21 | 88.8 | 8.1 | 0.1 | 0 | 3.0 |

The invention claimed is:

1. A process for converting lignin to liquid hydrocarbons, the process comprising:

hydrogenolyzing a lignin in the presence of at least one hydrogenolysis catalyst, selected from supported catalysts having formula (I), (II), (III), or (IV):

$$M^1/C \quad (I),$$

$$M^1/Al_2O_3 \quad (II),$$

$$M^2/SiO_2 \quad (III),$$

$$M^2/Al_2O_3 \quad (IV),$$

wherein $M^1$ is a metal selected from the group consisting of palladium, ruthenium, and platinum, and $M^2$ is nickel, at a temperature ranging from 250° C. to 350° C., to obtain a depolymerized lignin; and hydrodeoxygenating said depolymerized lignin in the presence of at least one hydrodeoxygenation catalyst selected from supported catalysts having formula (III), (V), (VI), (VII), or (VIII):

$$M^2/SiO_2 \quad (III),$$

$$M^3M/Al_2O_3 \quad (V),$$

$$M^3M/SiO_2{-}Al_2O_3 \quad (VI),$$

$$M^3MP/Al_2O_3 \quad (VII),$$

$$M^3MP/SiO_2{-}Al_2O_3 \quad (VIII),$$

wherein M is a metal selected from the group consisting of molybdenum and tungsten, $M^2$ is nickel, $M^3$ is a metal selected from the group consisting of cobalt and nickel, and P is phosphorous, at a temperature ranging from 300° C. to 500° C., to obtain a mixture of liquid hydrocarbons.

2. The process of claim 1, wherein said hydrogenolyzing temperature ranges from 290° C. to 320° C.

3. The process of claim 1, wherein said lignin is an Organosolv lignin.

4. The process of claim 1, wherein said lignin is a Kraft lignin.

5. The process of claim 1, wherein said lignin is selected from the group consisting of:
- a lignin that is a by-product from the production of ethanol from a lignocellulosic biomass;
- a lignin from an agricultural product or a waste product from the processing of said agricultural product; and
- a lignin from solid urban waste.

6. The process of claim 1, wherein said hydrogenolysis catalyst is a supported catalyst having a formula (I), (II), (III), or (IV):

$$M^1/C \quad (I),$$
$$M^1/Al_2O_3 \quad (II),$$
$$M^2/SiO_2 \quad (III),$$
$$M^2/Al_2O_3 \quad (IV),$$

wherein:
$M^1$ is palladium; and
$M^2$ is nickel.

7. The process of claim 1, wherein said hydrogenolysis occurs batchwise and said hydrogenolysis catalyst is present in a quantity ranging from 0.1% by weight to 20% by weight with respect to a total weight of said lignin.

8. The process of claim 7, wherein said hydrogenolysis catalyst is present in a quantity ranging from 1% by weight to 15% by weight with respect to the total weight of said lignin.

9. The process of claim 7, wherein said hydrogenolysis occurs batchwise in the presence of a solvent.

10. The process of claim 9, wherein said solvent is at least one selected from the group consisting of:
- a low-boiling solvent having a boiling point lower than or equal to 120° C.; and
- a hydroxy-aromatic solvent having a boiling point higher than or equal to 150° C.

11. The process of claim 10, wherein said solvent is a mixture of phenols obtained from hydrogenolysis of lignin carried out batchwise or continuously.

12. The process of claim 9, wherein said solvent is present in such a quantity as to have a solvent/lignin weight ratio lower than or equal to 20/1.

13. The process of claim 12, wherein said solvent is present in such a quantity as to have a solvent/lignin weight ratio ranging from 15/1 to 0.5/1.

14. The process of claim 7, wherein said hydrogenolysis occurs at a partial hydrogen pressure ranging from 1 MPa to 20 MPa.

15. The process of claim 14, wherein said partial hydrogen pressure ranges from 3 MPa to 15 MPa.

16. The process of claim 7, wherein said hydrogenolysis occurs over a time ranging from 9 minutes to 10 hours.

17. The process of claim 16, wherein said time ranges from 18 minutes to 5 hours.

18. The process of claim 1, wherein said hydrogenolyzing occurs continuously.

19. The process of claim 18, wherein said hydrogenolyzing occurs continuously in the presence of a solvent.

20. The process of claim 19, wherein said solvent is at least one hydroxy-aromatic solvent having a boiling point higher than or equal to 150° C.

21. The process of claim 20, wherein said solvent is a mixture of phenols obtained from hydrogenolysis of lignin carried out batchwise or continuously.

22. The process of claim 18, wherein said hydrogenolyzing occurs at a LHSV (Liquid Hourly Space Velocity) ranging from 0.2 hours$^{-1}$ to 6 hours$^{-1}$.

23. The process of claim 22, wherein said LHSV (Liquid Hourly Space Velocity) ranges from 0.25 hours$^{-1}$ to 3 hours$^{-1}$.

24. The process of claim 18, wherein said hydrogenolyzing occurs at a partial hydrogen pressure ranging from 1 MPa to 20 MPa.

25. The process of claim 24, wherein said partial hydrogen pressure ranges from 3 MPa to 15 MPa.

26. The process of claim 1, wherein said hydrodeoxygenating occurs in a single step or in multiple steps.

27. The process of claim 1, wherein said hydrodeoxygenating catalyst is a supported catalyst having formula (III), (V), (VI), (VII), or (VIII):

$$M^2/SiO_2 \quad (III),$$
$$M^3M/Al_2O_3 \quad (V),$$
$$M^3M/SiO_2-Al_2O_3 \quad (VI),$$
$$M^3MP/Al_2O_3 \quad (VII),$$
$$M^3MP/SiO_2-Al_2O_3 \quad (VIII),$$

wherein:
M is molybdenum,
$M^2$ is nickel,
$M^3$ is cobalt, or nickel, and
P is phosphorous.

28. The process of claim 27, wherein said metals M, $M^2$, and $M^3$ are deposited on the support of the supported catalyst in their sulphided form.

29. The process of claim 26, wherein said hydrodeoxygenating occurs batchwise and said hydrodeoxygenating catalyst is present in a quantity ranging from 0.1% by weight to 20% by weight with respect to a total weight of the depolymerized lignin.

30. The process of claim 29, wherein said hydrodeoxygenating catalyst is present in a quantity ranging from 1% by weight to 10% by weight with respect to the total weight of said depolymerized lignin.

31. The process of claim 29, wherein said hydrodeoxygenating occurs in the presence of at least one solvent selected from the group consisting of:
- a linear, branched or cyclic $C_{10}$-$C_{12}$ hydrocarbon having a boiling point ranging from 170° C. to 210° C.; and
- a hydroxy-aromatic solvent having a boiling point higher than or equal to 150° C.

32. The process of claim 31, wherein said solvent is a mixture of phenols obtained from hydrogenolysis of lignin carried out batchwise or continuously.

33. The process of claim 31, wherein said solvent is present in such a quantity as to have a solvent/depolymerized lignin weight ratio lower than or equal to 15/1.

34. The process of claim 33, wherein said solvent is present in such a quantity as to have a solvent/depolymerized lignin weight ratio ranging from 10/1 to 0.5/1.

35. The process of claim 29, wherein said hydrodeoxygenating occurs at a partial hydrogen pressure ranging from 1 MPa to 25 MPa.

36. The process of claim 35, wherein said hydrodeoxygenating occurs at a partial hydrogen pressure ranging from 3 MPa to 20 MPa.

37. The process of claim 29, wherein said hydrodeoxygenating occurs at a temperature ranging from 380° C. to 420° C.

38. The process of claim 29, wherein said hydrodeoxygenating occurs over a time ranging from 6 minutes to 10 hours.

39. The process of claim 38, wherein said hydrodeoxygenating occurs over a time ranging from 12 minutes to 5 hours.

40. The process of claim 1, wherein said hydrodeoxygenating occurs continuously.

41. The process of claim 40, wherein said hydrodeoxygenating occurs in the absence of a solvent.

42. The process of claim 40, wherein said hydrodeoxygenating occurs in the presence of a hydroxy-aromatic solvent having a boiling point higher than or equal to 150° C.

43. The process of claim 40, wherein said hydrodeoxygenating occurs at a LHSV (Liquid Hourly Space Velocity) ranging from 0.2 hours$^{-1}$ to 6 hours$^{-1}$.

44. The process of claim 43, wherein said LHSV (Liquid Hourly Space Velocity) ranges from 0.25 hours$^{-1}$ to 3 hours$^{-1}$.

45. The process of claim 40, wherein said hydrodeoxygenating occurs at a partial hydrogen pressure ranging from 1 MPa to 25 MPa.

46. The process of claim 45, wherein said partial hydrogen pressure ranges from 3 MPa to 20 MPa.

47. The process of claim 40, wherein said hydrodeoxygenating occurs at a temperature ranging from 380° C. to 420° C.

\* \* \* \* \*